(12) United States Patent
Sako et al.

(10) Patent No.: US 6,562,375 B1
(45) Date of Patent: May 13, 2003

(54) STABLE PHARMACEUTICAL COMPOSITION FOR ORAL USE

(75) Inventors: Kazuhiro Sako, Shizuoka (JP);
Toyohiro Sawada, Shizuoka (JP);
Keiichi Yoshihara, Shizuoka (JP);
Tatsunobu Yoshioka, Shizuoka (JP);
Shunsuke Watanabe, Shizuoka (JP)

(73) Assignee: Yamanouchi Pharmaceuticals, Co., Ltd., Tokyo (JP)

( * ) Notice: Subject to any disclaimer, the term of this patent is extended or adjusted under 35 U.S.C. 154(b) by 0 days.

(21) Appl. No.: 09/629,405

(22) Filed: Aug. 1, 2000

Related U.S. Application Data

(60) Provisional application No. 60/147,222, filed on Aug. 4, 1999.

(51) Int. Cl.$^7$ .............................. A61K 9/14; A61K 9/20
(52) U.S. Cl. ....................... 424/486; 424/464; 424/465; 424/482
(58) Field of Search ................................. 424/484, 473, 424/468, 469, 470, 486, 464, 465, 482

(56) References Cited

U.S. PATENT DOCUMENTS

| | | | |
|---|---|---|---|
| 4,859,470 A | | 8/1989 | Guittard et al. |
| 5,021,053 A | | 6/1991 | Barclay et al. |
| 5,532,003 A | * | 7/1996 | Wong et al. ................. 424/473 |
| 5,650,170 A | * | 7/1997 | Wright et al. ............... 424/467 |
| 6,117,453 A | * | 9/2000 | Seth et al. .................. 424/486 |

FOREIGN PATENT DOCUMENTS

| | | | |
|---|---|---|---|
| EP | 0 661 045 A1 | 9/1993 | ............ A61K/9/22 |
| EP | 661045 A1 * | 7/1995 | ............ A61K/9/22 |
| EP | 901787 | 3/1999 | |
| EP | 901787 A1 * | 3/1999 | ............ A61K/9/28 |
| JP | 4-346929 | 12/1992 | |
| JP | 5-92918 | 4/1993 | |

OTHER PUBLICATIONS

A pamphlet of Polyox® by Union Carbide.
A pamphlet of PEO by Seitetsu Chemical Ind.
English translation of p. 6 of the PEO pamphlet by Seitetsu Chemical Ind.

* cited by examiner

*Primary Examiner*—Thurman K. Page
*Assistant Examiner*—Robert M. Joynes
(74) *Attorney, Agent, or Firm*—Townsend and Townsend and Crew LLP

(57) ABSTRACT

The present invention is to provide a stable pharmaceutical composition for oral use and preparation thereof in which changes are prevented in drug release at stored even under the exposure to light by adding yellow ferric oxide and/or red ferric oxide in a matrix type sustained-release preparation containing a drug, hydrophilic base, and polyethylene oxide. The present invention is to further provide a method for preventing changes in drug release at stored under the exposure to light in a matrix type sustained-release preparation containing a drug, hydrophilic base, and polyethylene oxide. The quality assurance period of the product can be prolonged and the product value can be improved by the present invention.

21 Claims, No Drawings

STABLE PHARMACEUTICAL COMPOSITION FOR ORAL USE

CROSS-REFERENCES TO RELATED APPLICATIONS

This application claims priority to U.S. Ser. No. 60/147,222, filed Aug. 4, 1999, the disclosure of which is herein incorporated by reference in its entirety.

TECHNICAL FIELD

The present invention relates to a solid pharmaceutical composition for oral use with that prevents changes in drug release in a matrix type sustained-release preparation containing polyethylene oxide. The present invention also relates to a method of producing a stable solid pharmaceutical composition for oral use that prevents changes in drug release in a matrix type sustained-release preparation containing polyethylene oxide. Furthermore, the present invention relates to a method of preventing changes in drug release in a matrix type sustained-release preparation containing polyethylene oxide.

BACKGROUND OF THE INVENTION

Various sustained-release preparations have been developed in the field of pharmaceuticals, and release of the drug from this preparation is an important factor of preparation design in terms of in vivo absorption of the drug when the preparation is orally taken by the patient. Stable drug release from the preparation, wherein the release rate is steady with few changes, is essential, from the time the pharmaceutical preparation is made until it is transported, stored and orally taken by the patient.

Incidentally, various sustained-release preparations have been made by researchers affiliated with the applicant of the present patent. It goes without saying that, as with the main agent, in sustained-release preparations, the polymer substance that forms a hydrogel as the main base in particular must be also stable in order to maintain the rate with which the drug is released (WO 94/06414).

Polyethylene oxide can be mentioned as one polymer substance that forms a hydrogel. This substance is a water-soluble thermoplastic resin in the form of white powder or granules that is obtained by polymerization of ethylene oxide and that has a molecular weight of from several 100,000s to several 1,000,000s. It is known that because it is extremely sticky when wet, sustained-release preparations containing this substance show good drug release within the digestive tract. Although it is a known fact that the erosion rate of the polymer substance or a matrix made from said substance has a strong effect on this drug release rate, the factors that affect stability of the polyethylene oxide that is used as the base of sustained-release preparations, particularly factors that affect drug release, are not known.

The present inventors performed studies of polyethylene oxide as the base of sustained-release preparations, and they discovered that erosion of the matrix made from polyethylene oxide is accelerated when the preparation is preserved under exposure to light. As a result, the rate with which the drug is released increases over time, and there are changes in drug release. Therefore, the prevention of changes in drug release is desired.

DISCLOSURE OF THE INVENTION

The present invention provides a stable preparation that shows no changes in drug release in matrix type sustained-release preparations containing polyethylene oxide at the preserved period under exposure to light. Moreover, the present invention provides a method of producing a stable preparation with which there are no changes in drug release in matrix type sustained-release preparations containing polyethylene oxide. The present invention further provides a method with which changes in drug release are prevented in matrix type sustained-release preparations containing drugs and polyethylene oxide at the preserved period under exposure to light.

Under the above circumstances, the present inventors discovered that changes in drug release can be prevented at the preserved period even under exposure to light, if yellow ferric oxide or red ferric oxide, which has been used as coloring agent among pharmaceutical additives, was added by physical mixing in an amount of 10 wt %, which is in excess of the amount used as coloring agent (which said amount is very small and not more than 0.1 wt %) with drug and polyethylene oxide in a matrix type sustained-release preparation containing polyethylene oxide and was made into a tablet. The present inventors completed the present invention upon discovering that changes in drug release from a preparation can be prevented by adding yellow ferric oxide or red ferric oxide not only by means of physical mixing, but also by means of coating a tablet.

The mechanism of preventing effect by adding yellow ferric oxide or red ferric oxide has not been discerned, but it is thought that the mechanism is not just a prevention of the degradation of polyethylene oxide by exposure to light. That is, the present inventors found that titanium oxide absorbing light at the wavelength of not more than 400 nm (UV) and reflecting light at the wavelength of not less than 400 nm, or medicinal carbon absorbing light at all wavelength (broad range) cannot reduce changes in drug release in a matrix type tablet consisting of polyethylene oxide and polyethylene glycol even if it was added by physical mixing in an amount of 10 wt %, for example, per tablet weight. The anticipation that the stability against light can be performed if the wavelength (color) affecting the influence on the stability of polyethylene oxide is blocked. To the contrary, changes in drug release on the tablet could not be reduced even if all visual light was blocked by reflecting or by absorbing. This result suggested that the special wavelength affecting the influence on the stability in the visual region did not exist because the color of solution dissolving polyethylene oxide was colorless and clear. It had no absorbed wavelength in the visual region. If the special wavelength affecting the influence on the stability in visual region existed, the additive reflecting all visual light (white color) or the additive absorbing all visual light (black color) was anticipated to be able to make the stable preparation with no changes in drug release. To the contrary, it was an unexpected result. Therefore, although there is/are unknown factor(s) affecting changes in drug release besides light, the results suggested that yellow ferric oxide, which absorbs light at wavelength of not more than 400 nm and reflects light at wavelength of not less than 400 nm, or red ferric oxide, which absorbs light at wavelength of not more than 560 nm and reflects light at wavelength of not less than 560 run, could be added in an effective amount in a matrix type sustained-release preparation containing at least polyethylene oxide can reduce changes in drug release although the factor(s) affecting changes in drug release by compounding, by physical mixing or by coating tablet, may exist.

Accordingly, the present invention relates to 1) a stable pharmaceutical composition for oral use comprising a yellow ferric oxide and/or a red ferric oxide in an effective amount to stabilize a matrix type sustained-release preparation containing a drug, hydrophilic base, and polyethylene oxide. Moreover, the present invention relates to 2) the stable pharmaceutical composition for oral use according to the above-mentioned 1), wherein the amount of yellow ferric oxide and/or red ferric oxide added is not less than 0.3 wt % per tablet weight. The present invention also relates to 3) the stable pharmaceutical composition for oral use according to the above-mentioned 1) or 2), wherein the amount of yellow ferric oxide added is present from 1 to 20 wt % per preparation weight. In addition, the present invention relates to 4) the stable pharmaceutical composition for oral use according to the above-mentioned 1) or 2), wherein the amount of red ferric oxide added is present from 5 to 20 wt % per preparation weight. The present invention relates to 5) a method of producing a stable pharmaceutical composition for oral use comprising adding yellow ferric oxide and/or red ferric oxide in an amount effective to stabilize a matrix type sustained-release preparation to a mixture drug, hydrophilic base, and polyethylene oxide. Moreover, the present invention relates to 6) the method of producing a stable pharmaceutical composition for oral use according to the above-mentioned 5), wherein yellow ferric oxide and/or red ferric oxide is added by one or two or more means selected from film coating, granulation and mixing. Furthermore, the present invention relates to 7) the method of producing a stable pharmaceutical composition for oral use according to the above-mentioned 5) or 6), wherein the amount of yellow ferric oxide and/or red ferric oxide added is not less than 0.3 wt % per tablet weight. The present invention also relates to 8) a method of preventing changes in drug release by adding yellow ferric oxide and/or red ferric oxide in an amount effective to stabilize a matrix type sustained-release preparation containing a drug, hydrophilic base, and polyethylene oxide. The present invention further relates to 9) a use of yellow ferric oxide and/or red ferric oxide in an amount effective to stabilize a matrix type sustained-release preparation containing a drug, hydrophilic base, and polyethylene oxide in order to prevent changes in drug release.

The term 'a matrix preparation' signifies that it is a preparation that contains polyethylene oxide as a base of a sustained-release preparation, wherein a drug and hydrophilic base are dispersed in said polyethylene oxide.

There are no special restrictions to the drug used in the present invention as long as it is a drug used in sustained-release preparations that contain polyethylene oxide as one of its base components. Anti-inflammatory, antipyretic antispasmodics or analgesics such as indomethacin, diclofenac, diclofenac sodium, codeine, ibuprofen, phenylbutazone, oxyphenbutazone, mepirizole, aspirin, ethenzamide, acetaminophen, aminopyrine, phenacetin, butylscopolamine bromide, morphine, etomidoline, pentazocine, fenoprofen calcium, naproxen, selecxip, valdecxip, and tolamadol, anti-rheumatism drugs such as etodolac, anti-tuberculoses drugs such as isoniazide and ethambutol hydrochloride, cardio-vascular drugs such as isosorbide dinitrate, nitroglycerin, nifedipine, barnidipine hydrochloride, nicardipine hydrochloride, dipyridamole, amrinone, indenolol hydrochloride, hydralazine hydrochloride, methyldopa, furosemide, spironolactone, guanethidine nitrate, reserpine, amosulalol hydrochloride, lisinopril, metoprolol, pilocarpine, and talcetin, antipsychotic drugs such as chlorpromazine hydrochloride, amitriptyline hydrochloride, nemonapride, haloperidol, moperone hydrochloride, perphenazine, diazepam, lorazepam, chlorodiazepoxide, adinazolam, alprazolam, methylphenidate, myrnasipran, peroxetin, risperidone, and sodium valproate, anti-emetics such as metoclopramide, lamocetron hydrochloride, granisetron hydrochloride, ondansetron hydrochloride, and azacetron hydrochloride, antihistamines such as chlorpheniramine maleate and diphenhydramine hydrochloride, vitamins suh as thiamine nitrate, tocopherol acetate, cycothiamine, pyridoxal phosphate, cobarnamide, ascortic acid, and nicotinamide, anti-gout drugs such as allopurinol, colchicine, and probenecide, anti-Parkinson's disease drugs such as levodopa and selegrine, sedatives and hypnotics such as amobarbital, bromuralyl urea, midazolam, and chloral hydrate, antineoplastics such as fluorouracil, carmofur, acralvidine hydrochloride, cyclophosphamide, and thiodepa, anti-allergy drugs such as pseudoephedrine and terfenadine, decongestants such as phenylpropanolamine and ephedorine, diabetes mellitus drugs such as acetohexamide, insulin, tolbutamide, desmopressin, and glipizide, diuretics such as hydrochlorothiazide, polythiazide, and triamterene, bronchodilatos such as aminophylline, formoterol fumarate, and theophylline, antitussives such as codeine phosphate, noscapine, dimorfan phosphate, and dextromethorphan, anti-arrhythmics, such as quinidine nitrate, digitoxin, propafenone hydrochloride, and procainamide, topical anesthetics such as ethyl aminobenzoate, lidocaine, and dibucaine hydrochloride, anti-convulsants such as phenytoin, ethosuximide, and primidone, synthetic glucocorticoids such as hydrocortisone, prednisolone, triamcinolone, and betamethasone, antiulceratives such as famotidine, ranitidine hydrochloride, cimetidine, sucralfate, sulpiride, teprenone, plaunotol, 5-aminosalicylic acid, sulfasalazine, omeprazole, and lansoprazol, central nervous system drugs, such as indeloxazine, idebenone, thiapride hydrochloride, bifemelane hydrocide, and calcium homopantothenate, anti-hyperlipoproteinemics such as pravastatin sodium, simvastatin, lovastatin, and atorvastatin, antibiotics such as ampicillin hydrochloride, phthalylsulfacetamide, cefotetan, and josamycin, BPH therapeutic agents such as tamsulosin hydrochloride, doxazosin mesylate, and terazosin hydrochloride, drugs affecting uterine motility such as branylcast, zafylcast, albuterol, ambroxol, budesonide, and reproterol, peripheral circulation improvers of prostaglandin I derivatives such as beraprost sodium, anticoagulants, hypotensives, agents for treatment of cardiac insufficiency, agents used to treat the various complications of diabetes, peptic ulcer therapeutic agents, skin ulcer therapeutic agents, agents used to treat hyperlipemia, tocolytics, etc., can be mentioned as such a drug. The drug can be used in its free form or as a pharmaceutically acceptable salt. Moreover, one or a combination of two or more drugs can be used in the present invention.

There are no particular restrictions to the ratio in which the drug used in the present invention is added as long as it is the amount that is normally used pharmacologically for treatment or for prophylaxis, but it is preferably 85 wt % or less, particularly 80 wt % or less, of the entire preparation.

There are no special restrictions to the polyethylene oxide used in the present inventions as long as it can control release of the drug from the preparation. Examples of this polyethylene oxides (also referred to below as PEO) include POLYOX® WSR-303 (viscosity-average molecular weight: 7,000,000, viscosity: 7,500–10,000 cP (centipoise: 1% aqueous solution at 25° C.)), POLYOX® WSR Coagulant (viscosity-average molecular weight: 5,000,000, viscosity: 5,500–7,500 cP (1% aqueous solution at 25° C.)), POLYOX® WSR-301 (viscosity-average molecular weight: 4,000,000, viscosity: 1,650–5,500 cP (1% aqueous solution at 25° C.)), and POLYOX® WSRN-60K (viscosity-average molecular weight: 2,000,000, viscosity: 2,000–4,000 cP (2% aqueous solution at 25° C.)) (all made by Union Carbide), ALKOX® E-75 (viscosity-average molecular weight: 2,000,000 to 2,500,000, viscosity: 40–70 cP (0.5% aqueous solution at 25° C.)), ALKOX® E-100 (viscosity-average molecular weight: 2,500,000 to 3,000,000, viscosity: 90–110 cP (0.5% aqueous solution at 25° C.)), ALKOX® E-130 (viscosity-average molecular weight: 3,000,000 to 3,500,000, viscosity: 130–140 cP (0.5% aqueous solution at 25° C.)), ALKOX® E-160 (viscosity-average molecular weight: 3,600,000 to 4,000,000, viscosity: 150–160 cP (0.5% aqueous solution at 25° C.)), and ALKOX® E-240 (viscosity-average molecular weight: 4,000,000 to 5,000,000, viscosity: 200–240 cP (0.5% aqueous solution at 25° C.)) (all made by Meisei Kagaku (Chemical)), PEO-8 (viscosity-average molecular weight: 1,700,000 to 2,200,000, viscosity: 20–70 cP (0.5% aqueous solution at 25° C.)), PEO-15 (viscosity-average molecular weight: 3,300,000 to 3,800,000, viscosity: 130–250 cP (0.5% aqueous solution at 25° C.)), and PEO-18 (viscosity-average molecular weight: 4,300,000 to 4,800,000, viscosity: 250–480 cP (0.5% aqueous solution at 25° C.)) (all made by Seitetsu Kagaku (Chemical Industry) Co., Ltd.), etc. Moreover, the PEO used in the present invention preferably has a high viscosity at the time of gelling, or has a high viscosity-average molecular weight. This PEO is preferably, for instance, one with a viscosity of 2,000 cP or higher as an aqueous 2% solution (25° C.) or one that has a viscosity-average molecular weight of 2,000,000 or higher. One or a combination of two or more with different molecular weights, grades, etc., can be used as the PEO of the present invention.

There are no special restrictions to the ratio of polyethylene oxide added in the present invention as long as it is the amount with which release of drug from the preparation usually can be controlled. However, 10 to 95 wt % in terms of total preparation, or 15 to 90 wt % in terms of total preparation, is preferably used. The amount of PEO added is preferably 70 mg or more, particularly 100 mg or more, per 1 unit preparation.

The present invention relates to a pharmaceutical composition for oral use, wherein yellow ferric oxide and/or red ferric oxide are/is added in a matrix type sustained-release preparation containing a drug, hydrophilic base, and polyethylene oxide. The mechanism of this preparation is discussed in WO 94/06414. It is said that because the preparation absorbs water retained in the upper digestive tract and thereby almost completely gels (not less than 70%, preferably not less than 80%) and moves to the lower digestive tract as the surface of the preparation is being worn away with drug being released by further erosion, the drug is continually and thoroughly released and absorbed. As a result, sustained release performance is realized, even in the colon where there is little water.

There are no particular restrictions to said hydrophilic base as long as it can be dissolved before the polyethylene oxide used in the present invention gels. The amount of water needed to dissolve 1 g of this hydrophilic base is preferably 5 ml or less (at 20±5° C.), more preferably 4 ml or less (at the same temperature). Examples of said hydrophilic base include polyethylene glycol (for instance, Macrogol 400, Macrogol 1500, Macrogol 4000, Macrogol 6000, and Macrogol 20000 (all made by Nihon Yushi)), polyvinyl pyrrolidone (for instance, water-soluble polymers such as PVP® K30 (BASF)), sugar alcohols, such as D-sorbitol and xylitol, saccharides such as sucrose, maltose, lactulose, D-fructose, dextran (for instance, Dextran 40), and glucose, surfactants such as polyoxyethylene hydrogenated castor oil (for instance, Cremophor® RH40 (BASF) HCO-40, HCO-60 (Nikko Chemicals), polyoxyethylene polyoxypropylene glycol (for instance, Pluronic® F68 (Asahi Denka), etc.) or polyoxyethylene sorbitan higher fatty acid esters (such as Tween 80 (Kanto Kagaku(Chemical)), etc.), salts, such as sodium chloride and magnesium chloride, organic acids such as citric acid and tartaric acid, amino acids such as glycine, β-aniline, lysine hydrochloride, and amino saccharides such as meglumine, etc. Polyethylene glycol, sucrose and polyvinyl pyrrolidone are preferred and polyethylene glycol (particularly Macrogol 6000) is further preferred. Moreover, one or a combination of 2 or more hydrophilic bases can be used in the present invention.

When the hydrophilic base is added in the present invention, the ratio used is preferably 5 to 80 wt % per total preparation, particularly 5 to 60 wt %, per total preparation.

The yellow ferric oxide and/or red ferric oxide used in the present invention can be used alone or in combination.

There are no special restrictions to the ratio at which yellow ferric oxide and/or red ferric oxide of the present invention is added as long as it is an amount that can usually stabilize a matrix type sustained-release preparation and reduce the changes in drug release. This ratio differs depending on the type of substance and the method of addition, but it is preferably 1 to 20 wt %, particularly 3 to 15 wt %, with physical mixing in the matrix per preparation weight. For instance, as for red ferric oxide, it is preferably 5 to 20 wt %, particularly 10 to 15 wt %, per prepration weight. As for yellow ferric oxide, it is preferably 1 to 20 wt %, particularly 3 to 10 wt %, per preparation weight. When used in film coating, it is preferably 0.3 to 2 wt %, particularly 0.5 to 1.5 wt %, per tablet weight. The concentration of yellow ferric oxide or red ferric oxide contained in the film is preferably 5 to 50 wt %, particularly 10 to 20 wt %, per tablet weight. The term "physical mixing in the matrix" used here means a means with which, for instance, drug, polyethylene oxide and yellow ferric oxide and/or red ferric oxide are uniformly dispersed and as a result, the drug and yellow ferric oxide and/or red ferric oxide are uniformly dispersed in PEO as the main base of the sustained-release preparation. Moreover, the term "film coating" means that, for instance, yellow ferric oxide and/or red ferric oxide is dissolved or suspended in a water-soluble polymer solution of hydroxypropylmethyl cellulose, etc., and this is applied as a thin film to a tablet that has been separately prepared. Yellow ferric oxide and/or red ferric oxide of the present invention can be also contained as usual in the preparation. For instance, it can be added as a film by film coating, as granules by granulation or as part of the matrix (for instance, around the polyethylene oxide).

There are no special restrictions to the method of reducing changes in drug release from a pharmaceutical composition for oral use containing polyethylene oxide of the present invention as long as it means that said yellow ferric oxide and/or red ferric oxide will be added. For instance, film coating, granulation, mixing, etc. are mentioned. The means can be performed by one or by a combination of two or more.

Other additives that are pharmaceutically acceptable can be added as needed to the pharmaceutical composition of the present invention. For instance, one or a combination of two or more of fillers such as lactose, mannitol, potato starch, wheat starch, rice starch, corn starch, crystalline cellulose, methyl cellulose, gum Arabic, etc., viscosity-increasing agents, such as carboxymethyl cellulose, carboxymethyl cellulose calcium, carboxymethyl cellulose, etc., lubricants such as stearic acid, calcium stearate, magnesium stearate, talc, magnesium metasilicoaluminate, calcium hydrogen phosphate, anhydrous calcium hydrogen phosphate, etc., fluidizers such as silicon dioxide hydrate, light silic anhydride, dry aluminum hydroxide, etc., surfactants such as sodium laurylsulfate sucrose fatty acid esters, etc., coating agents such as zein, hydroxypropyl methyl cellulose, hydroxypropyl cellulose, etc., flavorings such as 1-menthol, mentha oil, fennel oil, etc., preservatives such as sodium sorbate, potassium sorbate, methyl parabenzoate, ethyl parabenzoate, etc., buffers such as citric acid, succinic acid, glycine, aspartic acid, alanine, arginine and its salts, magnesium oxide, zinc oxide, magnesium hydroxide, phosphoric acid, boric acid its salts, etc., can be added as needed.

There are no special restrictions to the method of producing pharmaceutical preparations consisting of the pharmaceutical composition of the present invention as long as it is a method that is usually suitable for hydrogel preparations. For instance, the tableting method whereby yellow ferric oxide and/or red ferric oxide and various additives, such as hydrophilic base, etc., as needed are mixed with the drug and PEO. This mixture may be compression molded, encapsulated under pressure, extrusion molded, or injection molded. Injection molding methods include, e.g., molding and curing after melting the mixture. In addition, coating, such as conventional sugar coating and film coating after molding, can be performed as needed. It is also possible to fill the product into capsules after molding.

BEST MODE FOR CARRYING OUT THE INVENTION

The present invention will now be explained in further detail while referring to a Comparative Example, Examples and Experiments, but the present invention is not limited to these descriptions.

Comparative Examples

| | |
|---|---|
| Polyethylene oxide (Polyox ® WSR303) | 150 (parts by weight) |
| Macrogol 6000 | 30 |

The polyethylene oxide and Macrogol 6000 were mixed with a mortar and pestle and made into tablets with an oil press at a tableting pressure of 1 ton/punch to obtain uncoated tablets with a diameter of 8 mm and tablet weight of 180 mg.

EXAMPLE 1

| | |
|---|---|
| Polyethylene oxide (Polyox ® WSR303) | 150 (parts by weight) |
| Macrogol 6000 | 30 |

The polyethylene oxide and Macrogol 6000 were mixed with a mortar and pestle and made into tablets with an oil press at a tableting pressure of 1 ton/punch to obtain tablets with a diameter of 8 mm and tablet weight of 180 mg.

Eight grams hydroxypropylmethyl cellulose 2910 (TC-5R) and 1.5 g Macrogol 6000 were dissolved in 88.5 g purified water and then 2.0 g yellow ferric oxide were dispersed in this to obtain the coating liquid. The uncoated tablets that had been made were coated with 3% of this solution per tablet weight using a film coating device HCT-mini, Freund Sangyo) to obtain the tablets of the present invention.

EXAMPLE 2

Film coating of uncoated tablets made in Example I was performed with the following coating solution:

Eight grams hydroxypropylmethyl cellulose 2910 (TC-5R) and 1.5 g Macrogol 6000 were dissolved in 88.5 g pure water and then 2.0 g red ferric oxide were dispersed in this to obtain the coating liquid. The uncoated tablets that had been made in Example 1 were coated with 3% of this solution per tablet weight using a film coating device (HCT-mini, Freund Sangyo) to obtain the tablets of the present invention.

EXAMPLE 3

Film coating of uncoated tablets made in Example 1 was performed with the following coating solution:

Eight grams hydroxypropylmethyl cellulose 2910 (TC-5R) and 1.5 g Macrogol 6000 were dissolved in 88.5 g pure water and then 2.0 g yellow ferric oxide and 0.5 g titanium oxide were dispersed in this to obtain the coating liquid. The uncoated tablets that had been made were coated with 3% of this solution per tablet weight using a film coating device (HCT-mini, Freund Sangyo) to obtain the tablets of the present invention.

EXAMPLE 4

Film coating of uncoated tablets made in Example 1 was performed with the following coating solution:

Eight grams hydroxypropylmethyl cellulose 2910 (TC-5R) and 1.5 g Macrogol 6000 were dissolved in 88.5 g pure water and then 2.0 g red ferric oxide and 0.5 g titanium oxide were dispersed in this to obtain the coating liquid. The uncoated tablets that had been made were coated with 3% of this solution per tablet weight using a film coating device (HCT-mini, Freund Sangyo) to obtain the tablets of the present invention.

EXAMPLE 5

| | |
|---|---|
| Polyethylene oxide (Polyox ® WSR303) | 150 (parts by weight) |
| Macrogol 6000 | 30 |
| Red ferric oxide | 20 |

The polyethylene oxide, Macrogol 6000 and red ferric oxide were mixed with a mortar and pestle and then made into tablets using an oil press at a tableting pressure of 1 ton/punch to obtain the tablets of the invention with a diameter of 8 mm and a tablet weight of 200 mg.

EXAMPLE 6

| | |
|---|---|
| Polyethylene oxide (Polyox ® WSR303) | 150 (parts by weight) |
| Macrogol 6000 | 30 |
| Yellow ferric oxide | 20 |

The polyethylene oxide, Macrogol 6000, and yellow ferric oxide were mixed with a mortar and pestle and then made into tablets using an oil press at a tableting pressure of 1 ton/punch to obtain tablets of the present invention with a diameter of 8 mm and tablet weight of 200 mg.

EXAMPLE 7

| | |
|---|---|
| Polyethylene oxide (Polyox ® WSR303) | 150 (parts by weight) |
| Macrogol 6000 | 30 |
| Yellow ferric oxide | 9.5 |

The polyethylene oxide, Macrogol 6000, and yellow ferric oxide were mixed with a mortar and pestle and then made into tablets using an oil press at a tableting pressure of 1 ton/punch to obtain tablets of the present invention with a diameter of 8 mm and tablet weight of 189.5 mg.

[Experiment] (Stability at the Preserved Period Under Exposure to Light)

The tablets obtained in the Comparative Example and Examples 1 through 7 were introduced to a plastic dish and exposed to light. Light exposure was performed by exposure to light for 8 weeks using Option 1 according to ICH guidelines (D65, which is the international standard for outdoor light in accordance with ISO10977) so that the total illumination intensity would be 1,200,000 Lux·hr. The following experiment was performed using tablets that had been exposed to light and tablets that had been stored for the same amount of time protected from light.

Matrix Erosion Experiment

The experiment was performed with a paddle speed at 200 rpm in accordance with Japan Pharmacopoeia Dissolution Experimental Methods, Method No. 2 (Paddle Method) using 500 ml purified water as the experimental solution. Six hours after starting the experiment, the tablets were removed from the flask and dried for 4 days in a dryer at 40° C. to evaporate the water content of the matrix tablet. The matrix erosion percentage was calculated from the difference between initial weight of the tablet and dry weight using formula (I) (Table 1).

Matrix erosion percentage=(initial weight−dry weight)/initial weight×100  (formula I)

TABLE 1

Matrix erosion experiment results

| | Percentage (%) eroded | |
|---|---|---|
| Preparation | Protected from light | Exposed to 1,200,000 Lux · h |
| Comparative Example 1 | 39.7 ± 0.4 | 57.4 ± 2.1 |
| Example 1 | 42.0 ± 0.3 | 42.6 ± 0.0 |
| Example 2 | 42.3 ± 1.0 | 41.5 ± 0.1 |
| Example 3 | 42.4 ± 0.5 | 42.8 ± 0.4 |
| Example 4 | 42.4 ± 0.5 | 42.8 ± 0.1 |
| Example 5 | 42.8 ± 0.5 | 47.7 ± 0.3 |
| Example 6 | 41.8 ± 0.2 | 41.6 ± 0.2 |
| Example 7 | 41.5 ± 0.4 | 42.8 ± 0.2 |

(n = 3, mean ± SD)

Results and Discussion

As shown in Table 1, it was estimated that the drug release rate of the Comparative Example in which the preparation did not contain yellow ferric oxide and/or red ferric oxide would increase with exposure to light because the matrix erosion percentage increased. The matrix erosion percentage was the same as with storage protected from light using film coating containing yellow ferric oxide or red ferric oxide. Moreover, acceleration of the matrix erosion percentage was controlled, and particularly strong results were realized with the addition of yellow ferric oxide, when physical mixing with yellow ferric oxide or red ferric oxide was performed.

Consequently, these results indicate that the pharmaceutical composition for oral use of the present invention to which yellow ferric oxide or red ferric oxide has been added is a stable preparation that shows no changes in drug release at the preserved period even under exposure to light.

Industrial Applicability

The pharmaceutical composition for oral use and the method of producing said composition in the present invention is to provide a stable preparation and a method of producing a stable preparation in which there is no changes in drug release in a matrix type sustained-release preparations containing polyethylene oxide, at the preserved period even under exposure to light.

The pharmaceutical composition for oral use is to provide a stable pharmaceutical composition for oral use by adding by means of coating or by physical mixture yellow ferric oxide and/or red ferric oxide, in which there is no changes in drug release. The method of stabilizing by means of mixture is to simplify the step of production processes, because the above mentioned substance can be added at granulated with polyethylene oxide and additives.

In addition, the method of the present invention is to provide a method of preventing changes in drug release in a matrix type sustained-release preparation containing a drug, hydrophilic base, and polyethylene oxide.

Therefore, the quality assurance period of the product can be expected to be prolonged and its product value can be increased as a result of stabilization of sustained-release preparations.

What is claimed is:

1. A stable hydrogel-forming pharmaceutical composition for oral use comprising:
    a yellow ferric oxide and/or a red ferric oxide in an amount effective to stabilize a matrix sustained-release preparation containing
        (a) a drug,
        (b) 5 to 80 wt % of hydrophilic base having a solubility that the amount of water needed to dissolve 1 g of said hydrophilic base is 5 ml or less at 20±5° C., and
        (c) 10 to 95 wt % of polyethylene oxide (i) having a viscosity of 2,000 cP or higher as an aqueous 2% solution at 25° C. or (ii) having a viscosity-average molecular weight of 2,000,000 or higher,
    wherein said matrix preparation contains polyethylene oxide as a base of a sustained-release preparation,
    wherein said drug and said hydrophilic base are dispersed in a polyethylene oxide, and
    wherein said amount of yellow ferric oxide is 1 to 20 wt % or red ferric oxide is 3 to 20 wt %, with physical mixing in the matrix per preparation weight, or said amount of yellow ferric oxide and/or red ferric oxide is 0.3 to 2 wt %, in film coating per tablet weight.

2. The stable hydrogel-forming pharmaceutical composition for oral use with improved stability according to claim 1, wherein said amount of yellow ferric oxide is 3 to 10, or red ferric oxide is 5 to 20 wt %, with physical mixing in the matrix per preparation weight.

3. The stable hydrogel-forming pharmaceutical composition for oral use with improved stability according to claim 2, wherein said amount of red ferric oxide is 10 to 15 wt % per preparation weight.

4. The stable hydrogel-forming pharmaceutical composition for oral use with improved stability according to claim 1, wherein said amount of yellow ferric oxide and/or red ferric oxide is 0.3 to 2 wt %, in film coating per tablet weight.

5. The stable hydrogel-forming pharmaceutical composition for oral use with improved stability according to claim 4, wherein said amount of yellow ferric oxide and/or red ferric oxide is 0.5 to 1.5 wt %, in film coating per tablet weight.

6. The stable hydrogel-forming pharmaceutical composition for oral use with improved stability according to claim 4 or 5, wherein the concentration in film material of a yellow ferric oxide and/or a red ferric oxide is 5 to 50%.

7. A method of producing a stable hydrogel-forming pharmaceutical composition for oral use with improved stability comprising adding a yellow ferric oxide and/or a red ferric oxide in an amount effective to stabilize a matrix sustained-release preparation to a drug, 5 to 80 wt % of hydrophilic base having a solubility that the amount of water needed to dissolve 1 g of said hydrophilic base is 5 ml or less at 20±5° C., and 10 to 95 wt % of polyethylene oxide having a viscosity of 2,000 cP or higher as an aqueous 2% solution at 25° C. or having a viscosity-average molecular weight of 2,000,000 or higher, wherein said matrix preparation contains polyethylene oxide as a base of a sustained-release preparation, wherein said drug and said hydrophilic base are dispersed in a polyethylene oxide, wherein said yellow ferric oxide with amount of 1 to 20 wt % or red ferric oxide with amount of 3 to 20 wt % is added to the preparation using granulation or mixing in the matrix per preparation weight, or said yellow ferric oxide and/or red ferric oxide with amount of amount of 0.3 to 2 wt % is added to the preparation in film coating per tablet weight.

8. The method of producing a stable hydrogel-forming pharmaceutical composition for oral use with improved stability according to claim 7, wherein said amount of yellow ferric oxide is 3 to 10 wt %, or red ferric oxide is 5 to 20 wt %, with physical mixing in the matrix per preparation weight.

9. The method of producing a stable hydrogel-forming pharmaceutical composition for oral use with improved stability according to claim 8, wherein said amount of red ferric oxide is 10 to 15 wt % per preparation weight.

10. The method of producing a stable hydrogel-forming pharmaceutical composition for oral use with improved stability according to claim 7, wherein said amount of yellow ferric oxide and/or red ferric oxide is 0.3 to 2 wt %, in film coating per preparation weight.

11. The method of producing a stable hydrogel-forming pharmaceutical composition for oral use with improved stability according to claim 10, wherein said amount of yellow ferric oxide and/or red ferric oxide is 0.5 to 1.5 wt %, in film coating per preparation weight.

12. The method of producing a stable hydrogel-forming pharmaceutical composition for oral use with improved stability according to claim 10 or 11, wherein the concentration in film material of a yellow ferric oxide and/or a red ferric oxide is 5 to 50%.

13. A method of preventing chances in drug release by adding yellow ferric oxide and/or red ferric oxide in an amount effective to stabilize a matrix sustained-release preparation containing a drug, a hydrophilic base, and a polyethylene oxide, wherein said matrix preparation contains said polyethylene oxide as a base of a sustained-release preparation, wherein said drug and said hydrophilic base are dispersed in said polyethylene oxide.

14. A method for increasing physical stability in an oral composition, said method comprising:

admixing a yellow ferric oxide and/or a red ferric oxide in an amount effective to stabilize a matrix sustained-release preparation containing a drug, a hydrophilic base, and a polyethylene oxide, wherein said matrix preparation contains said polyethylene oxide as a base of a sustained-release preparation.

15. The method for increasing physical stability in an oral composition according to claim 14, wherein yellow ferric oxide and/or red ferric oxide is added to the preparation using at least one of film coating, granulation and mixing.

16. The method for increasing physical stability in an oral composition according to claim 14 or 15, wherein said amount of yellow ferric oxide is 1 to 20 wt % or red ferric oxide is 3 to 20 wt %, with physical mixing in the matrix per preparation weight, or said amount of yellow ferric oxide and/or red ferric oxide is 0.3 to 2 wt %, in film coating per tablet weight.

17. The method for increasing physical stability in an oral composition according to claim 16, wherein said amount of yellow ferric oxide is 3 to 10 wt %, or red ferric oxide is 5 to 20 wt %, with physical mixing in the matrix per preparation weight.

18. The method for increasing physical stability in an oral composition according to claim 17, wherein said amount of red ferric oxide is 10 to 15 wt % per preparation weight.

19. The method for increasing physical stability in an oral composition according to claim 13 or 14, wherein said amount of yellow ferric oxide and/or red ferric oxide is 0.3 to 2 wt %, in film coating per preparation weight.

20. The method for increasing physical stability in an oral composition according to claim 19, wherein said amount of yellow ferric oxide and/or red ferric oxide is 0.5 to 1.5 wt % per preparation weight.

21. The method for increasing physical stability in an oral composition according to claim 19, wherein the concentration in film material of a yellow ferric oxide and/or a red ferric oxide is 5 to 50%.

* * * * *